United States Patent [19]

Schawaller

[11] Patent Number: 6,140,059
[45] Date of Patent: *Oct. 31, 2000

[54] METHODS FOR THE OBTENTION OF HUMAN IMMUNODEFICIENCY VIRSUS TYPE 1 ENVELOPE GLYCOPROTEINS IN NATIVE AND OLIGOMERIC FORM EMPLOYING RECOMBINANT CHIMERIC ANTIGENS CONTAINING COLLAGENASE RECOGNITION SITES.

[76] Inventor: Manfred Schawaller, Uhlandstrasse 20, D-75210 Keltern-Dietlingen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/448,619

[22] PCT Filed: Jan. 12, 1994

[86] PCT No.: PCT/DE94/00022

§ 371 Date: Sep. 29, 1995

§ 102(e) Date: Sep. 29, 1995

[87] PCT Pub. No.: WO94/16081

PCT Pub. Date: Jul. 21, 1994

[30] Foreign Application Priority Data

Jan. 16, 1993 [DE] Germany .............................. 43 01 017

[51] Int. Cl.[7] .................................................. G01N 33/53
[52] U.S. Cl. ...................... 435/7.1; 435/69.1; 435/69.3; 435/70.1; 530/350; 424/188.1; 424/208.1
[58] Field of Search ............................ 424/188.1, 184.1, 424/192.1; 435/69.1, 69.3, 70.1

[56] References Cited

PUBLICATIONS

Schawaller et al., "Studies with crosslinking regents on the oligomeric structure of the env glycoprotein of HIV,"Virol. 172:367–369, 1989.
Walker, J., "SDS polyacrylamide gel electrophoresis of proteins," The Protein Protocols Handbook, Walker, J. ed., Human Press Inc., Totowa, NJ pp. 55 and 61, 1996.
Sambrook et al., "SDS–polyacrylamide gel electrophoresis of proteins," in Molecular Cloning: A Laboratory Manual, Second Edition, Sambrook et al., Eds., Cold Spring Harbor Laboratory Press, Cold Spring Harbor, NY, p. 18.47, 1989.
Newman et al., "Immunological and formulation design considerations for subunit vaccines," in Vaccine Design: The Subunit and Adjuvant Approach, Powell et al., eds., Plenum Press, New York, pp. 1,2, and 17–28, 1995.

Haynes, B., "Scientific and social issues of human immunodeficiency virus vaccine development," Science 26:1279–1286, 1993.
Haynes et al., "Update on the issues of HIV vaccine development," Ann. Med. 28:39–41, 1996.
Jones et al., "Protein fold recognition," J. Comp.–Aided Molec. Design. 7(4):439–456. 1993.
Freimuth et al., "Introduction of guest peptides into *Escherichia coli* alkaline phosphatase," J. Biol. Chem. 265(2):896–901, 1990.
McWhirter et al., "A coiled–coil Oligomerization domain of Bcr is essential for the transforming function of Bcr–Abl oncoproteins," Molec. Cell. Biol. 13(12):7587–7595, 1993.
Defay et al., "Evaluation of current techniques for ab initio protein structure prediction," Proteins 23(3);431–45, 1995.
Willey et al., "Mutations within the human immunodeficiency virus type 1 gp 160 envelope glycoprotein alter its intracellular transport and processing," Virol. 184:319–329, 1991.
Modrow et al., 1987, J. Virol., 61:570–578.
Doms et al., 1991, "The Assembly of the HIV–1 Env Glycoprotein into Dimers and Tetramers", in Mechanisms and Specificity of HIV Entry into Host Cells, Düzgünes, N., ed., Plenum Press, New York, pp. 203–219.
Scholtissek et al., 1988, Gene 62:55–64.
Janvier et al., 1990, J. Virol. 64:4258–4263.
Bolognesi, D., 1990, TIBTECH 8:40–45.

*Primary Examiner*—Laurie Scheiner
*Assistant Examiner*—Jeffrey S. Parkin
*Attorney, Agent, or Firm*—Hardaway/Mann IP Group

[57] ABSTRACT

The present invention is relative to a method for the obtention of native domains of viral membrane proteins, especially of native, that is, oligomeric and glycosylated ectodomains of the surface protein gp160 of the human immunodeficiency virus HIV, the causative agent of AIDS (acquired immune deficiency syndrome), as well as the native protein domains themselves obtained by this method, especially native ectodomains of the env glycoprotein of HIV whose monomers exhibit an electrophoretic mobility of approximately 140 kD as well as their use as vaccine, especially as vaccine against HIV.

A nucleotide sequence coding for a recognition sequence for protein-splitting enzymes is inserted at a suitable site into the gene coding for the precursor protein of the protein domain to be obtained. After expression of the gene mutant in eukaryotic cells a digestion with a suitable enzyme is carried out and the protein domain to be obtained is subsequently purified.

23 Claims, 2 Drawing Sheets

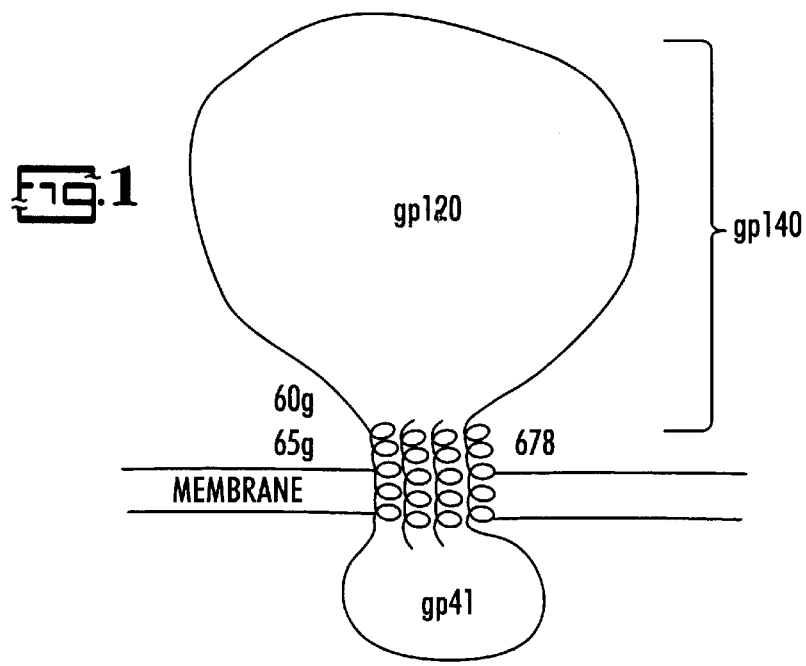

Fig. 1

```
                                        678 - Transmembranbereich - 702
                                        |                              |
        KNEQELLELDKWASLWNWFNITN    WLWYIKLFIMIVGGLVGLRIVFAVL    E1 (WT)

KNEQEFLELDKWASLWNWFNITN    WLWYIKLFIMIVGGLVGLRIVFAVL    E3 EcoR1)

KNEQELVPAGPRGPRGPKFLELDKWASLWNWFNITN    WLWYIKLFIMIVGGLVGLRIVFAVL    E3CA

KNEQELVAPAGPRGPRGPKFLELDKWASLWNWFNITN   WLWYIKLFIMIVGGLVGLRIVFAVL    E3CB

KNEQELVAAPAGPRGPRGPKFLELDKWASLWNWFNITN  WLWYIKLFIMIVGGLVGLRIVFAVL    E3CC
```

Fig. 2

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide"

(xi) SEQUENCE DESCRIPTION: SEQ ID NO:1:

GAACAAGAAT TCTTGGAATT AGATAAATGG 30

(2) INFORMATION FOR SEQ ID NO:2:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide"

(xi) SEQUENCE DESCRIPTION: SEQ ID NO:2:

AATTAGTTCC TGCCGGTCCA AGAGGTCCAA GGGGACCGA 39

(2) INFORMATION FOR SEQ ID NO:3:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "Oligonucleotide"

(xi) SEQUENCE DESCRIPTION: SEQ ID NO:3:

AATTTCGGTC CCCTTGGACC TCTTGGACCG GCAGGAACT 39

(2) INFORMATION FOR SEQ ID NO:4:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:4:

```
AATTAGCCGT ACCTGCCGGA CCGCGTCCAC CACGCGGACC TA                42
```

(2) INFORMATION FOR SEQ ID NO:5:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:5:

```
AATTTAGGTC CGCGTGGTCC ACGCGGTCCG GCAGGTACGG CT                42
```

(2) INFORMATION FOR SEQ ID NO:6:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:6:

```
AATTAGCAGC TGGTCCCGCA GGACCTCGCG GTCCTAGAGG TCCTA             45
```

(2) INFORMATION FOR SEQ ID NO:7:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:7:

```
AATTTAGGAC CTCTAGGACC GCGAGGTCCT GCGGGACCCA GCTGCT            46
```

(2) INFORMATION FOR SEQ ID NO:8:

(i) SEQUENCE CHARACTERISTICS:
        (A) LENGTH: 48 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

```
Lys Asn Glu Gln Glu Leu Leu Glu Leu Asp Lys Trp Ala Ser Leu Trp
1               5                   10                  15
```

```
Asn Trp Phe Asn Ile Thr Asn Trp Leu Trp Tyr Ile Lys Leu Phe Ile
                20                  25                  30

Met Ile Val Gly Gly Leu Val Gly Leu Arg Ile Val Phe Ala Val Leu
        35                  40                  45
```

(2) INFORMATION FOR SEQ ID NO:9:

(i) SEQUENCE CHARACTERISTICS:
        (A) LENGTH: 48 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:9:

```
Lys Asn Glu Gln Glu Phe Leu Glu Leu Asp Lys Trp Ala Ser Leu Trp
1               5                   10                  15

Asn Trp Phe Asn Ile Thr Asn Trp Leu Trp Tyr Ile Lys Leu Phe Ile
                20                  25                  30

Met Ile Val Gly Gly Leu Val Gly Leu Arg Ile Val Phe Ala Val Leu
        35                  40                  45
```

(2) INFORMATION FOR SEQ ID NO:10:

(i) SEQUENCE CHARACTERISTICS:
        (A) LENGTH: 61 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

```
Lys Asn Glu Gln Glu Leu Val Pro Ala Gly Pro Arg Gly Pro Arg Gly
1               5                   10                  15

Pro Lys Phe Leu Glu Leu Asp Lys Trp Ala Ser Leu Trp Asn Trp Phe
                20                  25                  30

Asn Ile Thr Asn Trp Leu Trp Tyr Ile Lys Leu Phe Ile Met Ile Val
        35                  40                  45

Gly Gly Leu Val Gly Leu Arg Ile Val Phe Ala Val Leu
    50                  55                  60
```

(2) INFORMATION FOR SEQ ID NO:11:

(i) SEQUENCE CHARACTERISTICS:
        (A) LENGTH: 62 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:11:

```
Lys Asn Glu Gln Glu Leu Val Ala Pro Ala Gly Pro Arg Gly Pro Arg
1               5                   10                  15

Gly Pro Lys Phe Leu Glu Leu Asp Lys Trp Ala Ser Leu Trp Asn Trp
                20                  25                  30

Phe Asn Ile Thr Asn Trp Leu Trp Tyr Ile Lys Leu Phe Ile Met Ile
        35                  40                  45

Val Gly Gly Leu Val Gly Leu Arg Ile Val Phe Ala Val Leu
    50                  55                  60
```

(2) INFORMATION FOR SEQ ID NO:12:

(i) SEQUENCE CHARACTERISTICS:
        (A) LENGTH: 63 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

```
Lys Asn Glu Gln Glu Leu Val Ala Ala Pro Ala Gly Pro Arg Gly Pro
1               5                   10                  15

Arg Gly Pro Lys Phe Leu Glu Leu Asp Lys Trp Ala Ser Leu Trp Asn
            20                  25                  30

Trp Phe Asn Ile Thr Asn Trp Leu Trp Tyr Ile Lys Leu Phe Ile Met
        35                  40                  45

Ile Val Gly Gly Leu Val Gly Leu Arg Ile Val Phe Ala Val Leu
    50                  55                  60
```

METHODS FOR THE OBTENTION OF HUMAN IMMUNODEFICIENCY VIRSUS TYPE 1 ENVELOPE GLYCOPROTEINS IN NATIVE AND OLIGOMERIC FORM EMPLOYING RECOMBINANT CHIMERIC ANTIGENS CONTAINING COLLAGENASE RECOGNITION SITES.

FIELD OF THE INVENTION

The present invention is relative to a method for the obtention of native domains of viral membrane proteins, especially of native ectodomains of the surface protein gp 160 of the human immunodeficiency virus HIV, the causative agent of AIDS (acquired immune deficiency syndrome), as well as the native protein domains themselves obtained by this method and their use as vaccine, especially the use of native ectodomains of the surface protein gp 160 of the human immunodeficiency virus HIV as vaccine against HIV. A method for determining suitable sites positions for the insertion of recognition sequences into the protein domains to be obtained, which function as enzymatic cleavage sites, especially as collagen splitting sites, as well as recognition sequences for collagenases themselves, is also a component of this method for the obtention of native domains of viral membrane proteins.

BACKGROUND OF THE INVENTION

A proven means for the prophylaxis of viral diseases is immunization, the vaccination of the body against the viruses. In earlier times viral diseases which occurred in epidemic fashion such as e.g. smallpox and polio were frequently able to be checked by means of vaccination. In order to achieve such an active immunization against a virus the body, more precisely the immune system, is exposed to a viral antigen. This can take place e.g. by injecting inactivated or attenuated viruses or also parts, e.g. of proteins of the virus. The human immune system is basically composed of two different partial systems, the cellular immunological response (T cells) and the humoral immunological response (B cells, antibodies). In the case of a reinfection with a virus the humoral immunological response, imparted by B cells, represents the most important defense mechanism.

The immune system of the body reacts to the antigen with the formation of specific antibodies which recognize and bind the antigen and therewith the virus, thus initiating its inactivation. In addition, so-called "memory cells" are formed, that is, special lymphocytes which are activated upon a later infection with "their" virus or "their antigen" and stimulate the immune system very rapidly to synthesize large amounts of the antigen-specific antibodies. In this manner the immune system can react significantly more rapidly to a viral attack than if it had never been confronted previously by the corresponding antigen.

However, the use of attenuated viruses for vaccination can be problematic in as far as it can not be excluded that the viruses used become virulent in the body again and an outbreak of the viral disease occurs. It is preferable for this reason to use an isolated protein of the virus as immunogen. For this, it is best to use a surface protein of the virus since it is normally readily accessible to the humoral immunological response. Ideally, only a part of a surface protein is used, namely, that part which is located externally on the virus surface, the so-called ectodomain, since in the case of the intact virus only this part is accessible to antibodies. However, care should be taken in the production of a protein domain to be used for vaccination against a virus that it should have the native form to the extent possible since otherwise there is the danger that antibodies are formed which do not recognize the native protein and therewith the virus and are therewith ineffective for neutralization. Such molecules or molecule parts which are recognized on the basis of their three-dimensional structure by antibodies are called conformational or structural epitopes and those which are recognized by their amino-acid sequence are called sequential epitopes. It turns out more and more that there are only very few sequential epitopes and that most antigenic epitopes are structural, that is, they must exhibit the correct three-dimensional folding of the polypeptide chain in order to be recognized by corresponding antibodies. "Native" means in this context that the spacial structure of the protein domain used is identical or nearly identical to the structure of the corresponding protein range occurring naturally on or in the virus. This includes, if necessary, the presence of oligomery and/or glycosylation of the protein domains. A significant criterion for this is the fact that antibodies which were formed against an isolated native, viral protein domain also recognize and bind the virus and the corresponding native protein in the virus.

The human immunodeficiency virus HIV, a retrovirus, poses great problems today. Since it was identified in 1984 as the cause of AIDS great efforts have been undertaken to produce a vaccine against this virus too. One has recently succeeded in successfully immunizing monkeys with attenuated SIV viruses (simian immunodeficiency virus), close relatives of HIV, which allows the supposition that humans could also be successfully immunized against HIV by means of attenuated HIV. The problem entailed by attenuated viruses as vaccines has already been addressed. In the case of a deadly disease like AIDS this risk that the attenuated virus becomes virulent again can not be accepted, even if it is very small. See in this regard also: Koff, W. C. and Hoth, D. F. in the journal "Science", 241, 426–432 (1988).

For this reason a great part of the research about HIV vaccines is concentrated on using individual proteins, especially the surface protein of the virus, the so-called gp 160, also called env-glycoprotein, or fragments thereof as antigen. (A general survey is offered by the article "AIDS-Impfstoffe" [German—AIDS Vaccines] by T. H. Matthews et al. in the journal "Spektrum der Wissenschaft", 12, 134–142 (1988).)

The env-glycoprotein of HIV, whose amino-acid sequence is known (Ratner et al., "Nature", 313, 277–284 (1985)), is first synthesized in the host cell as a highly glycosylated precursor protein gp 160 and subsequently processed in a Golgi's body to the two domains gp120 and gp41. The gp120 domain, which is located externally on the virus membrane, is responsible for the binding to the cellular receptor CD4 and both gp120 and precursor protein gp160 bind with high affinity to this CD4 receptor. Gp41, which exhibits a transmembrane domain, participates in the fusion of viral and cellular membrane during the penetration of the virus into the cell, probably by means of the interaction of a "fusion peptide" located on the amino terminus of gp 41, with the lipid double layer of the host cell membrane.

The approach of using only the external part of the env glycoprotein for the development of an HIV vaccine appears to be quite promising. This is based on the consideration already mentioned that the part of the glycoprotein which is exposed to the outside is the most easily accessible to the humoral immunological response and therefore an immunization against this ectodomain is the most promising.

The obtention of the ectodomain of the HIV surface protein can take place in various ways. It can e.g. be "cut off" by mechanical, chemical or enzymatic methods from the virus coating. The danger is great thereby that the protein is denatured and results in the formation of antibodies which recognize the native surface protein and therewith the virus only poorly or not at all.

Robey et al. ("Proc. Natl. Acad. Sci. USA", 83, 7023–7027 (1986)) obtain gp120 e.g. by removing the protein from the surface of HIV-infected cells by means of the rather strong detergent Triton X100. Even if the authors call their preparation "native gp120", it is doubtful in light of the detergent used and the purification methods used whether the gp120 obtained in this manner is actually present in native and oligomeric form.

A genetic engineering method consists in that a stop codon is inserted quasi as "theoretical breakage site" shortly before the start of the gp41 gene. During the expression of the gene in suitable cells the position of the stop codon then determines the position of the carboxy terminal end of the ectodomain of the surface protein, that is, only the external part of the surface protein, the domain gp 120, is synthesized. However, when synthesized in this manner gp 120 is present as a monomer, which does not correspond to the natural conditions on the virus since the env glycoprotein is present, like most viral glycoproteins in native form, as oligomer. Frequently, these proteins are trimers; it was recently able to be demonstrated for the HIV-1-env glycoprotein that it is a tetramer in native form (Schawaller, M. et al., "Virology", 172, 367–369 (1989). This explains why monomeric gp120 does not result in suitable antibodies and can therewith be poorly utilized as vaccine. Even experiments of the inventor in which gp 120 was synthesized from cells which had been infected with a recombinant vaccinia virus by means of which the env is expressed, showed that gp 120 is not formed in a stable manner in oligomeric form. The test results indicate that gp41 must be present during the biosynthesis of the env glycoprotein in order to assure the oligomerization. The domain of gp41 responsible for this oligomerization is probably located within the 129 amino terminal amino acids of gp41 (Earl, P. L. et al. "Proc. Natl. Acad. Sci. USA", 87, 648–652 (1990)).

Since gp41 is obviously of great significance in the synthesis of native gp160, experiments have also been undertaken to produce the complete gp160 in stable form. Barret et al. ("AIDS Research and Human Retroviruses" 5, (2), 159–170 (1989)) obtain gp160 e.g. by expressing the env gene in eukaryotic cells and subsequent purification; however, in addition to detergents they also use potassium thiocyanate, which has a strong chaotropic action and denatures proteins. Papers of the author have shown that the pure preparation of gp160 posed great problems for the following reasons:

Gp160 is, as described above, a membrane protein. Detergents are necessary for dissolving this protein out of the membrane. They are also necessary since isolated gp160 molecules aggregate in the absence of detergents. However, detergents result in a change of the molecule. It was determined that gp160 with detergents exhibits a change of the protease digestive pattern in comparison to the untreated protein. When the detergent is removed out of the solution, which is necessary at the latest when the protein is to be injected into a patient e.g. for the purpose of vaccination, the oligomer decomposes to the monomer. For the reasons cited, the chances of being able to produce pure gp160 in native form appear to be very slim.

The essential disadvantage which all previous methods for developing a vaccine against HIV on the basis of the isolated ectodomain of the env glycoprotein have in common is thus most likely the fact that the protein used as immunogen was not present in native and oligomeric form. This becomes clear from the fact that the titers indicated by the authors, which were determined by ELISA, are very high (around 1/100,000) and on the other hand the titers measured in the neutralization test are extremely low (often far less than 1/1000). This suggests that the antigens used in each instance do exhibit a strong immunogenic action, thus, a large amount of antibodies are formed against them, but that these antibodies hardly recognize or do not recognize at all the native protein and therewith the virus either.

The low titers in the neutralization test show that antibodies recognizing the native antigen are present only in very low titers. However, low-titer antibodies frequently result in an elevation of the virus infectivity (Prabhakar et al., Nature, 290, 590 (1981)). In other words, instead of protecting the host from the infection, the infectivity is increased by virus-specific immunoglobulins. In this instance the vaccine has the opposite of the desired effect as a consequence. The problem described also results in the case of all other viruses comprising a surface membrane with membrane-bound proteins.

In addition to their use as vaccine native proteins and protein domains are also used as immunotherapeutic agent or for diagnostic purposes. For diagnosis both antigens and also the antibodies directed against them are used.

SUMMARY OF THE INVENTION

The technical problem underlying the present invention is to provide a method for the obtention of native domains of viral membrane proteins, especially of native ectodomains of the env glycoprotein gp160 of the human immunodeficiency virus which can be used e.g. as vaccine for immunotherapy or diagnostic purposes. This problem also comprises providing a method for identifying a suitable site for the insertion of a recognition sequence for protein-splitting enzymes, especially collagenases, into viral membrane proteins, e.g. into the HIV-env glycoprotein gp160 as well as the making available of a suitable collagenase splitting site.

This problem is solved in that a method for the obtention of domains of viral membrane proteins in native form is made available which is characterized in that A nucleotide sequence coding for an amino acid sequence which represents a recognition sequence, especially for proteases or glycolipid anchors, is inserted at a suitable site into the gene coding for the protein containing the desired protein domain and The gene mutant obtained in this manner is expressed in eukaryotic cells and These eukaryotic cells or parts of them which contain the desired protein domain are subjected to an enzymatic digestion, preferably by a protease which recognizes and cleaves the inserted recognition sequence and The desired protein domain is obtained from the mixture.

Generally speaking, this means that at first a nucleotide sequence representing a recognition sequence for protein-splitting enzymes, especially proteases or glycolipid anchors, is first inserted at a suitable site into the gene coding for the initial form (e.g. gp160), the precursor protein of the protein domain to be obtained. After completed synthesis of the protein by means of suitable eukaryotic cells it is split at the inserted recognition sequence with the corresponding enzymes and subsequently the desired protein domain is purified. When the HIV env glycoprotein gp160 is used as precursor protein oligomeric, especially tetrameric glycoproteins result from this method whose monomers exhibit an electrophoretic mobility of approximately 140 kD and which are called gp140 in the following.

BRIEF DESCRIPTION OF THE DRAWINGS

FIG. 1 is a schematic of the HIV env-glycoprotein illustrating the transmembrane domain in a portion of the surface membrane of a virus.

FIG. 2 are amino acid sequences of the products of wild-type env genes showing a collagenase splitting site.

DETAILED DESCRIPTION OF THE INVENTION

Figure 3:
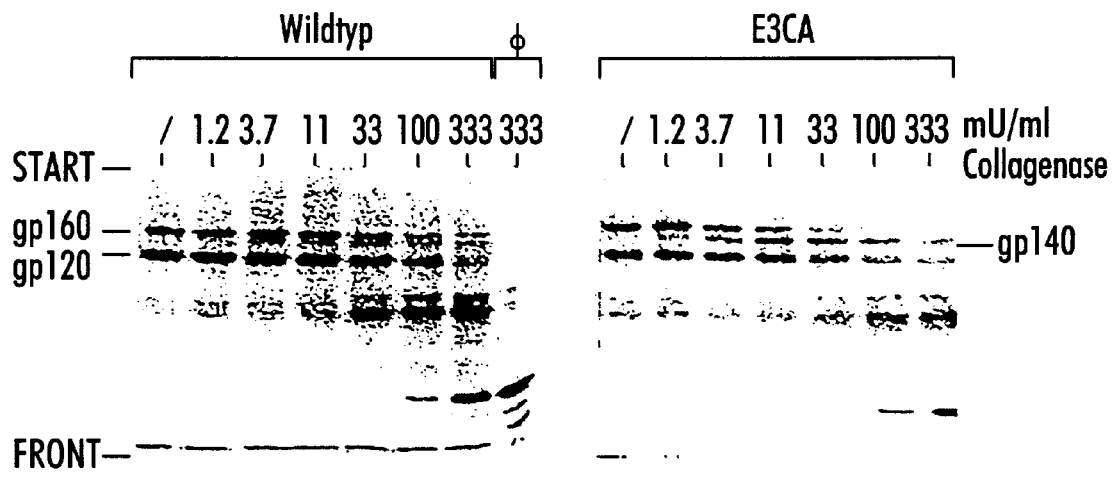
FIG. 3 is a photographic record of a polyacrylamide gel assay comparing wild-type and mutated env proteins.

The invention is therefore based on the idea of first synthesizing the complete protein, since it can be synthesized in native and oligomeric form only in this manner, and after the completed synthesis, of splitting off the desired protein domain enzymatically at a specific site. The corresponding gene is manipulated in such a manner beforehand that the finished protein contains an additional amino acid sequence which serves as recognition sequence for protein-splitting enzymes or for glycolipid anchors. This additional sequence does not change the native protein structure. The desired protein domain is obtained in native and oligomeric structure by means of enzymatic splitting of the entire protein on this recognition sequence. According to its nature this recognition sequence is an amino acid sequence which is recognized and split by proteases; however, it can also be a recognition sequence for lipid anchors, in which instance a purposeful splitting is likewise possible by means of lipases (see in this connection: Ferguson, M. A. J.; "Ann. Rev. Biochem.", 57, 285–320 (1988)).

In the first step of the method of the invention the area in the protein which is suitable for the insertion of a recognition sequence must be identified at first. This takes place by means of a method called "Pepscan". Then, a recognition sequence for an endonuclease, e.g., EcoRI is produced in the gene sequence corresponding to the identified protein range into which the sequence coding for the desired amino acid sequence—the recognition sequence in the protein—is inserted. Instead of EcoRI any other endonuclease can be used; however, no other similar recognition sequences should be present in the near vicinity of the recognition sequence of this endonuclease since otherwise the cloning efficiency can decrease. The gene obtained in this manner is inserted into a vector, e.g. a plasmid which is transfected ("introduced") into suitable eukaryotic cells which then synthesize the entire protein including the inserted recognition sequence. In this manner the entire protein is obtained in native, oligomeric and glycosylated form. Then the desired domain is separated from the rest of the protein with a suitable enzyme which cuts the protein at the inserted recognition sequence. The desired protein domain is subsequently purified by means of suitable purification methods such as e.g. affinity chromatography, ion exchange chromatography or gradient centrifugation. Referring to the splitting ("proteolytic") enzyme used, the essential criterion for its suitability is the fact that it recognizes the splitting ("cleavage") site by its amino acid sequence. This condition is met by bacterial collagenases, also sporadic vegetable collagenases as well as e.g. the blood coagulating factor Xa.

In a preferred embodiment of the invention the natural processing sequence of the precursor protein is destroyed in order to raise the yield. This takes place e.g. by exchanging one or more amino acids in the processing sequence. This has the consequence that the precursor protein, in the case of HIV the gp160, is not split up into the individual domains (in HIV, therefore, gp41 and gp120).

The precursor protein is synthesized in the rough endoplasmatic reticulum (RER) of the cell. The protein is not processed, that is, split up into the individual domains, until in the Golgi's apparatus, thus, during the transport to the cell surface. If the processing sequence of the precursor protein is destroyed, not only the amount of precursor protein which is still present in the RER at the time of the membrane preparation is obtained but also in addition the unprocessed precursor protein already transported to the cell surface.

In a further preferred embodiment of the invention the introduction of the mutant gene into the eukaryotic cell does not take place by means of a plasmid but rather by means of a recombinant virus, especially by means of a recombinant vaccinia virus. The use of a recombinant vaccinia virus as vector is particularly advantageous for the production of rather large amounts of the desired viral protein domains. The particular gene mutant can be inserted e.g. into the thymidine kinase gene of the vaccinia virus. Since the probability for such a recombination is about $1/1000$ to $1/10,000$, it is advantageous to select for the recombinant virus after the recombination. This can take place e.g. by using the mutagen bromodesoxyuridine in HTK cells. Only the wild-type vaccinia virus (TK$^+$) inserts this mutagenic nucleotide derivative into the DNA and the amount of the recombinant viruses (TK$^-$) is about 90% after two selections already. High protein yields are obtained when using a late promotor, e.g. the cowpox 160K promotor, which is a strong vaccinia promotor (Patel, D. D. et al., "Proc. Natl. Acad. Sci. USA", 85, 9431–9435 (1988)). A survey of the use of the vaccinia virus as vector for the expression of genes in the cytoplasm of eukaryotic cells is offered by Moss, B. ("Science", 252, 1662–1667 (1988)).

Further specifications regarding the method of the invention, a recognition sequence in accordance with the invention and the native protein domains of the invention and their use constitute subject matter of the subclaims.

The invention, which is sketched above in a quite general manner, was made during the investigation of the structure of the env glycoprotein of HIV; however, it can be used in principle in the case of all viruses comprising an envelope membrane. It was necessary for crystallization experiments with the ectodomain of the env glycoprotein to produce this ectodomain in the native, oligomeric form without the hydrophobic, transmembrane domain. However, the oligomerization process of type I viral glycoproteins is probably a function of the presence of this hydrophobic, transmembrane domain during the biosynthesis. Moreover, the folding of the polypeptide chain seems to be influenced by the fact that the polypeptide chain is membrane-bound during the synthesis. In order to obtain the ectodomain of the env glycoprotein in native form the entire mutant env glycoprotein was synthesized in COS cells at first after the insertion of a sequence coding for a collagenase splitting site into the env gene and thereafter the desired ectodomain was split off by a bacterial collagenase from the synthesized total protein and subsequently purified.

The identifying of a suitable site in the protein for the insertion of the collagenase splitting site, the recognition sequence, proved to be a big problem thereby. It turned out that there is only a very small area in the protein at which the recognition sequence can be inserted and the protein can then also be split with success. During a purely empirical determination of such a suitable site more than 30 different env gene mutants had to be produced in which the recognition sequence was inserted at different sites in the desired region of gp41 in order to find a site at which the desired proteolytic splitting was possible.

The numbering of the amino acids of the HIV env glycoprotein and of the bases of the HIV env gene used in the following refers to the numbering employed by Ratner (Ratner et al., "Nature", 313, 277–284 (1985)).

The precise spacial-structure of the env glycoprotein is not known; the structure of the area of the protein in which the protease splitting site can be logically inserted is constructed as follows (see FIG. 1 also):

If one starts from hydrophobicity profiles of gp41, the first amino acid of the transmembrane area is Trp 678 in the opinion of the inventor. However, the profession is not in agreement about the precise position of the transmembrane area of gp41. Bolognesi, P. D. ("Mol. Biol. Med.", 7, 1–15 (1990) assumes, for example, that the transmembrane area of gp160 extends from amino acid 691 to amino acid 712. It is clear that the four preserved glycosylation sites of gp41 localized at positions 611, 616, 624 and 637 must be aminoterminal to the transmembrane domain, thus, in the ectodomain. Furthermore, conclusions can be made about the secondary structure of gp41 from UV circular dichroism measurements on purified gp120 and gp160 preparations. These measurements have shown that gp120 consists almost exclusively of P-pleated-sheet structures whereas gp160 exhibits approximately 30% α-helical areas. This suggests that the secondary structure of gp41 is essentially an α-helix. In addition, it can be concluded from sequence analyses of the env gene of different HIV strains that the region in gp41 between Pro 609 and the transmembrane area (Trp 678) also has a-helical structure. This assumption is further supported by the fact that none of the HIV strains between Pro 609 and Trp 678 investigated has a proline, which would probably interrupt the α-helical structure. If the results of the inventor and of others are also included, namely that the HIV env glycoprotein is a tetramer, it can be imagined that four long, amphiphatic α-helices form an intertwined helical structure (coiled-coil) and that the particular hydrophobic regions of the subunits interact with each other, stabilizing the oligomeric structure of gp41 thereby. In this model the hydrophilic amino-acid side chains are located externally on a tetrameric helix and different amino acids can be present in the case of different strains.

Building on the previously named hypotheses, the region between the last glycosylation site in amino acid 637 and the beginning of the transmembrane domain was selected for the insertion of the recognition sequence, a section at any rate 40 to 53 amino acids long, according to where the beginning of the transmembrane ares is assumed to be. It is essential for the functionality of the recognition sequence that it must be readily accessible for the corresponding splitting enzyme.

On the basis of this recognition that the localization of a suitable site for the insertion of a recognition sequence is essentially a function of the accessibility of the corresponding protein area for the splitting enzyme, a novel method was developed for the identification of a suitable insertion site for a recognition sequence which method constitutes subject matter of claims 4–7.

Since antibodies against a protein can only be formed against those structures which are located on the outside of the protein, which are thus accessible to the cells of the immune system, and since the accessibility is also a significant criterion for a functioning recognition sequence, suitable areas in the protein for the insertion of recognition sequences can be identified in that those epitopes are identified against which antibodies are formed after immunization with the particular protein. P. Horal and coworkers have employed the so-called "Pepscan" method for investigating against which areas of the HIV-1-env glycoprotein gp41 antibodies are formed at all (see P. Horal et al. in the journal "J. Virol.", 65, 2718–2723 (1991)). This method is used differently in the present invention than in Horal et al. for the identification of the suitable area in the protein for the recognition sequence. For this, in principle small fragments of the protein are mixed with antibodies which were obtained by immunizing a mammal with the entire protein. In practice, the protein is not decomposed into fragments but rather for the sake of simplicity peptides overlapping in correspondence with the protein sequence with a length of 5 to 30, especially 12 to 16 amino acids are synthesized. These peptides are compounded with serum from HIV-1-positive patients. The antibodies present in this serum react with those peptides which are accessibly located on the surface in the case of the native protein and which thus represent potential insertion sites for recognition sequences. This method can identify the best-suited section in the protein for the insertion of a recognition sequence in accordance with the length of the peptides used up to an range of a few amino acids. In order to find the precise, optimal site, as many protein mutants are produced and tested as is necessary in order to exactly localize the optimal site for the recognition sequence in the previously identified area. In the case of the env glycoprotein of HIV-1 the best-suited site for the insertion of a collagenase splitting site is located between the amino acids Leu 659 and Leu 660 (see FIG. 2). Based on the colinearity of gene sequence and protein sequence this corresponds to nucleotides A 7778 and T 7779 of the env gene. Starting from this site the insertion of a collagenase splitting site is likewise possible in a range of 17 amino acids at a time in the direction of the C terminus and the N terminus; as the distance increases, one must reckon with lesser yields of splitting products and therewith of the desired protein domain.

A further problem was posed by the determining of the structure of a suitable splitting site. There are rather few proteases which split polypeptides sequence-specifically. Examples for highly specific proteases are bacterial, sporadically also vegetable collagenases or the blood coagulation factor Xa. Also, recognition sequences for glycolipid anchors are suitable in principle. A complicating matter is the fact that most endoproteases, differently than e.g. DNA restriction endonucleases, must rely for the recognition of the splitting site not only on the sequence but also on specific secondary or tertiary structures of the substrate, which are, however, not known. Furthermore, the recognition sequence must not be too large in order to be able to exclude the structure of the entire protein from being significantly influenced by its size.

A short, collagen-like sequence of the general form

—(G—P—X)$_n$— in which n>1, especially 3 and X is one of the 20 amino acids determined by the genetic code is best suited as recognition sequence (claim 4).

A similar sequence is suggested in German patent application DE 37 31 874 but as part of a fusion protein. In contrast to the present invention the goal followed in application DE 37 31 874 is to produce especially small proteins and peptides in fermentation processes. However, since just particularly such peptides are exposed in an intensified fashion to a proteolytic degradation in the cell, it is suggested that the peptide be synthesized as part of a greater fusion protein together with a bacterial amino-acid sequence and a collagen-like sequence in a bacterial host cell and subsequently split with a bacterial collagenase.

Using the collagen-like sequence cited, three different HIV-1-env gene mutants (E3CA, E3CB, E3CC) were produced whose expression product can be specifically split by means of a bacterial collagenase in the desired manner. Using these mutants, ectodomains of the env glycoprotein can be obtained as water-soluble, oligomeric, especially tetrameric glycoproteins whose monomers exhibit an electric mobility of approximately 140 kD and are therefore called gp140. These proteins consist of the domain gp120 and a part of the domain gp41 (claims 11 to 14). Since they no longer exhibit a transmembrane domain, no strong detergents which could change the native structure of the glycoproteins are necessary for cleaning up these glycoproteins, otherwise than in the cleaning of complete gp 160. Clear evidence for the fact that gp140 has oligomeric structure results on the one hand from sedimentation analyses (FIG. 4; see in this connection also Earl, P. L. et al., "Proc. Natl. Acad. Sci. USA" 87, 648–652 (1990)) and on the other hand from cross-linking experiments (re this methodology see Schawaller, M. et al., "Virology", 172, 367–369 (1989)). The obtention of oligomeric gp140 using the env gene mutant E3CA is explained in detail in the following example of an embodiment in conjunction with FIGS. 1 to 4:

FIG. 1 shows a schema of the HIV env glycoprotein with the transmembrane domain in the surface membrane of the virus. The numbers indicate the position of the amino acids according to the nomenclature of Ratner et al., "Nature", 313, 277–287 (1985)). Domain gp41 begins at amino acid 512, which, however, is difficult to localize in such a schema.

FIG. 2 (SEQ ID NOS 8–12, respectively) shows sections of the amino-acid sequences of the products of wild-type env gene (E1(WT)) of the BH10 clone and of various mutants. The changes in the mutants in comparison to the wild-type env product are underlined.

FIG. 3 shows the specific splitting of the wild-type env- and of the E3CA env protein by different concentrations of bacterial collagenase. The products obtained were analyzed by immunoblotting after gel electrophoretic separation on 6% SDS polyacrylamide gel and by subsequent detection with polyclonal rabbit serum against gp120. An autoradiography took place thereafter using a radioactively marked, secondary antibody directed against rabbit immunoglobulins (Amersham IM 134).

Figure 4:
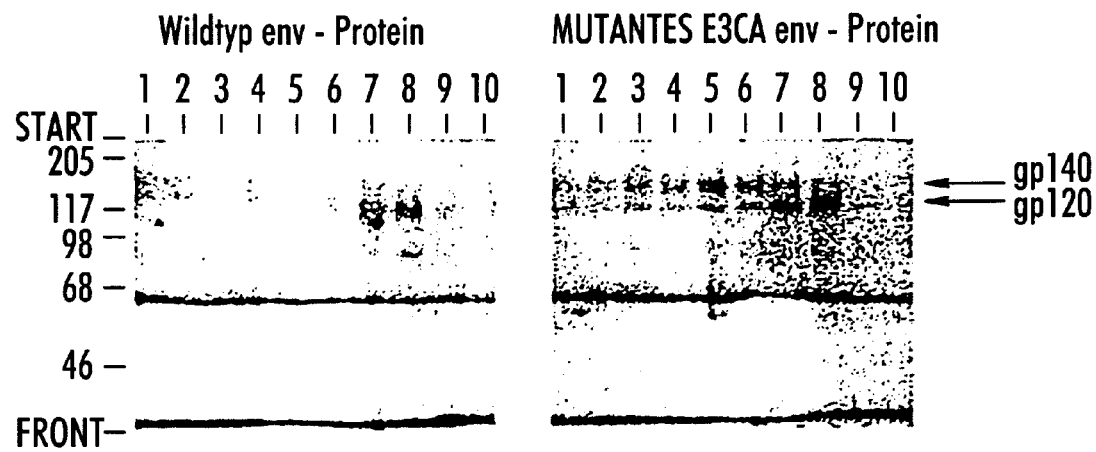
FIG. 4 is a record of a sedimentation analysis of the products of the collagenase digestion of wild-type and mutant membranes.

FIG. 4 shows a sedimentation analysis of the products of the collagenase digestion of wild-type- and E3CA mutant membranes. Collagenase concentration: 200 mU/ml, 37° C., 3h. The products obtained were layered on a preformed 5 to 20% sucrose gradient in 10 mM HEPES, pH 7.8, 150 mM NaCl and centrifuged in an SW41 rotor (Beckmann) for 16 h at 35,000 rpm and 5° C. Ten fractions were harvested, starting from the bottom of the tube, and analyzed by immunoblotting.

The construction of the env gene mutants E3CA, E3CB, E3CC is illustrated in FIG. 2, in which the sequence of the wild-type env gene (El) is shown in the transmembrane domain and the region situated aminoterminally to the transmembrane domain. A single cleavage site for the endonuclease EcoRI was produced at the position coding for Leu 659 by a point mutation, as a result of which Leu is replaced by Phe in the protein. The product resulting therefrom is the env gene mutant E3. A base sequence was inserted into this new EcoRI cleavage site which sequence codes for the following amino-acid sequence (for the abbreviation of amino acids see e.g. A. L. Lehninger, Biochemie, VCH-Verlag Weinheim, 1987):

VPAGPRGPRGPKF (residues 7–19 of SEQ ID NO:10)

This sequence 13 amino acids long represents a collagenase recognition and splitting site. The product with this insert was named E3CA. The oligonucleotide 39 base pairs long and coding for this sequence was synthesized with a DNA synthesizing apparatus of the Applied Biosystems company. For the production of the env gene mutants as well as their cloning in an expression vector see also T. Maniatis et al., Molecular Cloning, Cold Spring Harbor, N.Y., USA (1982).

Construction of the env gene mutants a: Destruction of the processing sequence:

In order to increase the yield, the natural processing sequence of the env gene product was destroyed at first. Adenosine 7334 was replaced by cytosine (A 7334 C) in the plasmid pVB4 (Bosch, V. and Pawlita, M., "J. Virol", 64, 2337–2344 (1990)), which brings about a replacement of arginine 511 by serine (Arg 511 Ser) in the protein.

Plasmid pVB4 altered in this manner was combined thereafter with the E3CA plasmid containing the protease splitting site (see under c:). To this end the 5 end of pVB4 (SalI/HindIII fragment) was ligated with the 3 end of the E3CA plasmid (HindIII/XhoI fragment) and cloned into the p-bluescript.

b: Site-directed mutagenesis:

A gene from BH10 env (SalI/XhoI fragment was cloned into an M13 vector. Re the BH10 clone see Ratner et al., "Nature" 313, 277–284 (1985). The mutagenesis to the production of the EcoRI recognition sequence took place according to t. Kunkel et al. ("Meth. Enzymol.", 154, 367–382 (1987)) with the oligonucleotide MAN 5: (SEQ ID NO:1

```
5' GAA CAA GAA TTC* TTG AAA TTA GAT AAA TGG 3'
           659 660
```

The mutagenized base A 7781C is marked with an asterisk and the EcoRI recognition site is bolded. The numbers indicate the position of the corresponding amino acids in the env gene product.

The verification took place by means of sequencing. The env gene mutant obtained in this manner is designated as E3 (BH10,A7781C).

c: Insertion of complementary oligonucleotides:

The EcoRI recognition sequence contained in the bluescript pks+ was destroyed by opening by means of EcoR I, filling up by DNA polymerase I (Klenow fragment) and connecting the ends by ligase. Then, env E3 was subcloned into bluescript pks+. Then, E3 was linearized with EcoRI and cleaned via an agarose gel.

The insertion of the sequence 39 nucleotides long and coding for the collagenase splitting site took place now into this EcoRI recognition site of E3:

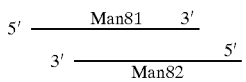

The mutant obtained in this manner is named E3CA. Two further mutants were produced using the complementary oligonucleotide sequences Man83 and Man84 (E3CB) as well as Man85 and Man86 (E3CC). These oligonucleotide sequences are presented in the following: (SEQ ID NOS 2–7, respectively)

Man81:
  5'-AATTAGTTCCTGCCGGTCCAAGAGGTCCAAGG GGACCGA-3'
Man82:
  5'-AATTTCGGTCCCCTTGGACCTCTTGGACCGGC AGGAACT-3'
Man83:
  5'-AATTAGCCGTACCTGCCGGACCGCGTGGACCA CGCGGACCTA-3'
Man84:
  5'-AATTTAGGTCCGCGTGGTCCACGCGGTCCGGC AGGTACGGCT-3'
Man85:
  5'-AATTAGCAGCTGGTCCCGCAGGACCTCGCGGT CCTAGAGGTCCTA-3'
Man86:
  5'-AATTTAGGACCTCTAGGACCGCGAGGTCCTGC GGGACCAGCTGCT-3'

For the insertion of the complementary oligonucleotides into the EcoRI recognition site in E3 the oligonucleotides were mixed in 150 mM NaCl, TE (10 mM Tris, 0.1 mM EDTA, pH 8) (1:1, mole:mole). The mixture was then heated 2 h at 95° C. and then allowed to cool off for 30 min to room temperature. The ligase reaction took place thereafter together with linearized E3 (pks+) with a high excess of the particular oligonucleotide pair. The plasmids produced in this manner were transformed in *Escherichia coli* DH5 and analyzed by sequencing. The yield of newly recombinant plasmids is over 90%.

d: Cloning into the expression vector pSVL:

In order to express the env genes they were cloned into the expression vector pSVL (Pharmacia, Uppsala, Sweden) (the unique BamHI recognition site had been deleted previously in pSVL). pSVL was linearized with XhoI and the env genes subcloned as SalI/XhoI fragment (BH 10 clone). The env genes were placed under the control of the SV40 late promotor.

A further possibility of producing an expression vector containing the various genes consists in the so-called PCR (polymerase chain reaction) constructing. A survey of this methodology can be found in Jones, D. H. et al., "Nature", 344, 793–794 (1990).

The env gene mutants E3CB and E3CC were produced for the following reason: There was a reasonable possibility that the alignment of the collagenase cleavage site within the α-helix could have an influence on the ability to function. Since in an α-helix three amino acids constitute approximately one complete revolution of the helix, the alignment of the collagenase splitting site within the α-helix was shifted by about 1200 and by about 2400, respectively, by inserting one amino acid alanine (E3CB) and two amino acids alanine (E3CC), respectively. However, the mutants E3CB and E3CC obtained in this manner led to the same positive result as the E3CA mutant.

The expression of the various env genes was carried out in COS 7 cells. COS 7 cells are fibroblasts; however, in principle all eukaryotic cells could be used instead such as e.g. CV1 cells, yeast cells, insect cells (Summers, M. D. and Smith, G. E.: A Manual of Methods for Baculovirus Vectors and Insect Cell Culture Procedures. Texas Agricultural Experiment Station, Bulletin No. 1555, (1988)) etc. The COS 7 cells were transformed with the PSVL plasmids by electroporation and subsequently incubated 48 h in complete growth medium (Gluzman, Y. et al., "Cell", 23, 175–182 (1981)). Thereafter, the cells were harvested and the env proteins analyzed. All current methods can be used for the transformation of the cells with the expression vector but in the present instance electrophoresis yields especially good success rates between 10 and 50%.

Electroporation:

Approximately 107 ($2\times10^6$–$5\times10^7$) COS 7 cells in a logarithmic growth phase were trypsinated and washed with DMEM (Dulbecco Modified Eagles' Medium). For electroporation the cells were compounded with 5–30 gg pSVL in DMEM and electroporated in a BioRad Gene Pulser (room temperature; 800 μl; 250 V; 500 μF; 0.4 cm cell.

For the analysis whether the collagenase splitting leads to the desired success, that is, whether after collagenase treatment of the mutant E3CA a native ectodomain of the env glycoprotein (gp140) can be extracted, membrane preparations were produced after hypotonic cellular lysis by means of sucrose density centrifugation (Schawaller, M. et al., "Virology" 172, 367–369 (1989)).

Cleaning of the membrane preparation:

Wash membrane preparation several times, take up in HEPES buffered saline (HBS: 10 mM HEPES pH 7.8; 150 mM NaCl): +1/10 vol. 10× HBS, +1/100 vol. 1 M $CaCl_2$, +1/5 vol. 20% β-D-octylglucoside at 37° C. Then treatment with Potter. Incubate several hours at 37° C. Then centrifuge for 30 min. at 100,000×g and 37° C. The supernatant obtained was then subjected to a protease digestion with purified collagenase (EC 3.4.24.3) from Clostridium histolyticum (Sigma C0773, Deisenhofen) in concentrations between 1.2 and 333 mU/ml.

Collagenase digestion:

The collagenase digestion was carried out in the following buffer for 3 h at 37° C.:

300 mM NaCl
20 mM HEPES (hydroxyethylpiperazine ethane sulfonic acid), pH 7.8
10 mM $CaCl_2$
50/M $ZnCl_2$
4% β-D-octylglucoside The following protease inhibitors can be added to this buffer in order to minimize unspecific proteolysis:

| | |
|---|---|
| 1 μM E64 | (cysteine protease inhibitor) |
| 1 μM pepstatine A | (aspartyl protease inhibitor) |
| 1 mM PMSF (phenylmethyl-sulfonylfluoride) | (serine protease inhibitor) |

Instead of β-D-octylglucoside, other mild detergents such as CHAPS or DOC (deoxycholate) can also be used. For the action of various detergents on membrane proteins see also Womack, M. D. et al., "Biochim. Biophys. Acta", 733, 210–215 (1983).

The optimum collagenase concentration is between 50 and 250 mU/ml (3 h, 37° C.), at higher concentrations unspecific digestion products occur in an intensified fashion and the yield of desired product, a 140 kD glycoprotein, becomes less.

Purification of a 140 kD env glycoprotein (gp140):

a: Lentil lectin affinity chromatography: The proteolysed fraction was diluted 1:1 with distilled water and placed on a Lentil lectin sepharose 4B column (Pharmacia 17-0444-0'). The mixture was then washed with 5 column volumes HBS, 2% β-D-octylglucoside, then with 5 column volumes HBS and then with 5 column volumes 10 mM HEPES (pH 7.8), 50 mM NaCl. The mixture was then eluted with 500–1000 mM α-D-methylmannoside in 10 mM HEPES, 50 mM NaCl (optional warming to 37° C.). Regarding lentil lectin affinity chromatography see also Hayman, M. J. et al., "FEBS Letters", 29 (2), 185–188 (1973).

The eluate was then concentrated. Gp140 is now present in a purity of about 50–70%.

b: Mono Q FPLC: The eluate from a: was taken up in 10 mM BTP (bis-trispropane), 50 mM $H_3BO_4$, pH 8.2 and placed on a Mono Q HR 5/5 column (Pharmacia); the protein concentration was approximately 1 mg/ml thereby. The column was eluted with an NaCl gradient of 30–600 mM for 40 min., 0.5–1 ml/min., UV monitor at 280 nm. Analysis by SDS PAGE Coomassie and/or Western blot. The gp140 env protein elutes at about 400 mM NaCl. Gp140 is now present in a purity of about 80–90%. The addition of $H_3BO_4$ (borate) to the buffer has the advantage that this hinders the aggregating of the glycoproteins. This hindering of the aggregation of the glycoproteins by $H_3BO_4$ is probably based on a complexing of the vicinal hydroxyl groups frequent in glycoproteins (claim 8). The borate can be present in the buffer at a concentration of from about 1 to about 200 mM, and is preferably present at a concentration of from about 30 to about 100 mM.

c: Sucrose density centrifugation: Approximately 1 ml eluate from b: was loaded from above onto a preformed sucrose gradient 5–20% in HBS (10 mM HEPES, pH 7.8; 150 mM NaCl) and centrifuged in a SW41 rotor (Beckmann) at 35,000 rpm, 16 h, 5° C. Then, 10 fractions were removed (from the bottom upward). In fraction 5, gp140 has a purity of 90–95%. Analysis took place by SDS PAGE and/or Western blot. Since no Ca ions are contained in the buffer during the centrifugation e.g. phosphate buffer can also be used instead of HEPES buffer.

The proteolysis products were analyzed by means of SDS-PAGE (sodium laurylsulfate polyacrylamide gel electrophoresis) and subsequent immunoblotting using a polyclonal rabbit serum, directed against gp120, which recognizes both gp120 as well as gp160.

The immunoblot (Western blot) in FIG. 3 shows that the wild-type env gene (clone BH10) and the mutant E3CA empress approximately equal amounts of gp160. Obviously, the proteolytic processing of gp160 to gp120 and gp41, which takes place in a Golgi's apparatus, also occurs in the same manner in the case of wild-type env and mutant env protein if the processing sequence is intact. After treatment with bacterial collagenase the E3CA env protein resulted in a novel digestion product whose monomeric form exhibits an electrophoretic mobility of about 140 kD which was not found in the digestion of the wild-type env protein. This digestion product is the desired native ectodomain of the env glycoprotein. The electrophoretic mobility of the novel digestion product, which is somewhat less with 140 kD than that of gp120, results from the fact that the collagenase splitting site was inserted in the case of amino acid 659 of the entire protein gp160 in the area of domain gp41. Domain gp120 ends at amino acid arginine 511 (see FIG. 1 also). The newly produced, native ectodomain of the HIV-1-env glycoprotein, gp140, thus consists of the entire domain gp120, a partial piece, 148 amino acids long, of domain gp41 as well as of the piece of the collagen-like sequence remaining after collagenase digestion. This last-named piece, which forms the C-terminal end of the glycoprotein, is indeed a type of foreign body in the glycoprotein of the invention but does not disturb its function. It can be removed but does not absolutely have to.

The electrophoretic mobility of gp120 of the wild-type env- and of the E3CA env protein is not changed by the collagenase treatment. This shows that the collagenase splitting site inserted in mutant E3CA is specifically recognized and split by the bacterial collagenase.

A further proof for the fact that the collagenase splitting site inserted in mutant E3CA is specifically recognized and split by the bacterial collagenase follows from the results of the sedimentation analysis of the collagenase splitting products (FIG. 4). Membrane preparations of COS 7 cells which express the wild-type gene or the E3CA-env gene were extracted with 4% β-D-octylglycoside and digested as described above with collagenase. The digestion products obtained were centrifuged by means of sucrose density centrifugation over a preformed 5%–20% sucrose gradient in 10 mM HEPES, pH 7.8, 150 mM NaCl in the absence of detergents for 16 h at 35,000 rpm in an SW41 rotor (Beckmann). Then, a total of ten fractions were removed and tested by SDS-PAGE and immunoblotting for their content of env proteins. gp120 was found again in both instances in fractions 7 and 8, which corresponds to the monomeric gp120 with a sedimentation coefficient of 7S. In contrast thereto, the digestion product of 140 kD, which occured only in the case of the E3CA mutant and not of the wild type, was found again in fraction 5, which corresponds to a coefficient of sedimentation of 11S.

In a preferred embodiment a recombinant vaccinia virus (VV) is used as expression vector. The construction of this recombinant vaccinia virus is described in detail in the following example of an embodiment.

The vaccinia shuttle plasmid p2100 was used as initial material (Patel, D. D. et al., "Proc. Natl. Acad. Sci. USA", 85, 9431–9435 (1988)). In addition to bacterial origin and resistance gene it contains the following gene fragment:

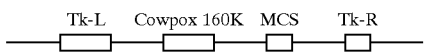

Tk-L=left arm of the thymidine kinase gene
Tk-R=right arm of the thymidine kinase gene
cowpox 160K=promotor/enhancer sequences
MCS=multiple cloning site By means of cloning double-stranded oligonucleotides 3' to a promotor, a Lac O sequence, 24 bp palindrome, was inserted and the MCS expanded by several unique endonuclease recognition sites. The Lac O sequence is necessary to suppress the transcription in E. coli to a minimum.

The particular env gene (wild type or mutant: from pks plasmid) was cloned into the new restriction sites (e.g. E3CA) (re the methodology see Chakrabarti, S. et al., "Molec. Cell Biol.", 5, 3403–3409 (1985)).

The following construct is obtained:

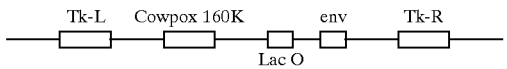

For the production of recombinant vaccinia viruses the plasmids were analyzed by restriction analysis and partial sequencing. The plasmids were transfected ("introduced") into CV 1 cells by electroporation (conditions as with COS-7 cells, see the first example of an embodiment) and infected with wild type VV (Copenhagen strain (multiplicity of infection (MOI)<1). Recombinant VV by means of which the env gene can be expressed are produced by homologous recombination in the thymidine kinase gene of the plasmid with the thymidine kinase gene of the VV with a probability of about 1/1000–1/10000. Since they are phenotypically TK⁻ they can be positively selected by 5'-bromodeoxyuridine (BdUR) selection in HTK cells. Two rounds of BdUR/HTK⁻ selection and subsequent "plaqueing" (the identifying of plaques and the removal of recombinant VV) from CV 1 cells yields approximately 50–90% env-expressing plaques (VV env) which can be identified by Western blot of a 1 ml culture. Another plaqueing results in the desired recombinant vaccinia virus by which env can be expressed.

Use of the viral membrane protein domains:

The native domains of viral membrane proteins in accordance with the invention can be used as vaccine against viruses. To this end they are administered to the patient preferably in combination with suitable adjuvants. However, any buffer components such as e.g. HEPES which may still be contained must be removed beforehand. This can take place e.g. by means of dialysis against physiological solution of common salt in phosphate buffer.

Furthermore, the native domains of the viral membrane proteins can be used for immunotherapy.

The native, viral protein domains are also suitable for diagnostic purposes. For the one, they can serve as antigen e.g. in immunoassays for demonstrating specific antibodies and for the other, they can also be used to obtain antibodies, both monoclonal and also polyclonal antibodies, which can then serve for a direct demonstration of the virus.

A further important purpose of the cleaned-up, native domains of viral membrane proteins is their use for crystallization. If the protein is present in crystalline form the three-dimensional structure can be determined. This is especially interesting because it makes it possible to clarify the exact structure of the binding pocket. If this structure is known, it is perhaps possible to construct inhibitors, that is, rather small molecules which fix exactly into this binding pocket and to block therewith the binding of the protein, that is, of the virus, to the CD4 molecule, the receptor of the host cell.

What is claimed is:

1. A method for the production of recombinant truncated HIV envelope glycoprotein gp140 domains that retain their native oligomeric and glycosylated form comprising the following:

(i) providing a nucleotide sequence encoding an amino acid sequence comprising a protease recognition site;

(ii) providing a nucleotide sequence encoding for the HIV envelope glycoprotein precursor gp160, wherein said sequence lacks a functional wildtype gp120/gp41 proteolytic cleavage site;

(iii) inserting the nucleotide sequence of step (i) into the nucleotide sequence of step (ii) at a region corresponding to amino acids 645 to 673 of the transmembrane area of gp41, wherein said numbering scheme is based upon isolate HXB2, thereby creating a mutant HIV envelope gene;

(iv) cloning the mutant HIV envelope gene into a suitable expression vector and expressing said mutant HIV envelope gene in eukaryotic cell line to produce a recombinant mutant HIV envelope glycoprotein gp160 comprising said protease recognition site;

(v) subjecting the expression product of step (iv) to enzymatic digestion with a suitable protease thereby creating HIV gp140 envelope glycoprotein domains that retain their native oligomeric and glycosylated form; and (vi) isolating and purifying said HIV gp140 from the digestion mixture.

2. The method according to claim 1 wherein said recognition sequence is a recognition sequence for proteases, lipases, or blood coagulating factor Xa.

3. The method according to claim 1 wherein said recognition sequence has the following general form:

$$—(G—P—X)_n—$$

in which n is a whole number greater than 1 and X is one of the 20 amino acids determined by the genetic code, said recognition sequence being specific for a collagenase.

4. The method according to claim 1 further comprising supplying a buffer to the enzymatic digestion products of said enzymatic digestion, said buffer comprising borate in a concentration between 1 and 200 mM.

5. The method according to claim 3, wherein said collagenase is a bacterial collagenase.

6. The method according to claim 1 wherein said desired protein domain is an ectodomain of the env-glycoprotein of HIV.

7. The method according to claim 1 comprising the additional step of inserting said recognition sequence into said nucleotide region coding for said HIV env-glycoprotein between amino acids 659 and 660.

8. The method according to claim 4, wherein said concentration is from 30 to 100 mM.

9. The method according to claim 1 wherein a suitable insertion site is identified by the following method:

(i) synthesizing short, overlapping oligopeptide sequences corresponding to the amino acid sequence of wildtype HIV gp160;

(ii) admixing said oligopeptides with HIV gp160-specific antiserum under conditions that facilitate the formation of peptide-antibody complexes;

(iii) identifying those oligopeptide sequences that are antigenic and correspond to surface accessible domains, said surface accessible domains providing suitable insertion sites for the proteolytic cleavage site, within the region corresponding to amino acids 645 to 673 of the transmembrane area of gp41, wherein said numbering scheme is based upon isolate HXB2.

10. The method according to claim 9, wherein said overlapping peptide sequences have a length of between 5 and 30 amino acids.

11. The method according to claim 9, wherein each of said overlapping olipopeptide sequences has a length of 12 to 16 amino acids.

12. The protein domains isolated according to the method of claim 1 comprising: HIV env-glycoproteins in native oligomeric and glycosylated form.

13. The protein domains according to claim 12, wherein said protein domains are ectodomains.

14. The isolated protein domains according to claim 13, wherein said protein domains are in tetrameric form.

15. The isolated protein domains according to claim 13, wherein the monomeric form of said protein domains has an electrophoretic mobility of about 140 kD as measured by 6% SDS-PAGE analysis.

16. The isolated protein domains according to claim 15, said protein domains comprising: domain gp120 of the HIV env-glycoprotein and the aminoterminal portion of domain gp41 of the HIV env-glycoprotein said aminoterminal portion further comprising an aminoterminal amino acid sequence having a length in the range of from 131 to 165 amino acids following said enzymatic digestion.

17. The protein domains according to claim 16, wherein said length of said aminoterminal amino acid sequence is 148 amino acids.

18. A method for diagnosing the presence or absence of an antibody-mediated immune response by a mammal to the presence of HIV env-glycoprotein comprising:

mixing protein domains isolated in accordance with the method of claim 1 with serum from said mammal to form a reaction mixture;

maintaining said reaction mixture under conditions conducive to the formation of antibody-antigen complexes;

analyzing said antibody-antigen complexes to determine the presence or absence in said antibody-antigen complexes of said protein domains.

19. A method for the production of immunogenic, recombinant truncated HIV envelope glycoprotein gp140 domains that retain their native oligomeric and glycosylated form and that are capable of inducing HIV-specific immune responses comprising the following:

(i) providing a nucieotide sequence encoding an amino acid sequence comprising a protease recognition site;

(ii) providing a nucleotide sequence encoding for the HIV envelope glycoprotein precursor gp160, wherein said sequence lacks a functional wildtype gp120/gp41 proteolytic cleavage site;

(iii) inserting the nucleotide sequence of step (i) into the nucleotide sequence of step (ii) at a region corresponding to amino acids 645 to 673 of the transmembrane area of gp41, wherein said numbering scheme is based upon isolate HXB2, thereby creating a mutant HIV envelope gene;

(iv) cloning the mutant HIV envelope gene into a suitable expression vector and expressing said mutant HIV envelope gene in a eukaryotic cell line to produce a recombinant mutant HIV envelope glycoprotein gp160 comprising said protease recognition site;

(v) subjecting the expression product of step (iv) to enzymatic digestion with a suitable protease thereby creating HIV gp140 envelope glycoprotein domains that retain their native oligomeric and glycosylated form;

(vi) isolating and purifying said HIV gp140 from the digestion mixture; and (vii) mixing said gp140 with a suitable adjuvant wherein said gp140 maintains a spatial and multimeric configuration that is substantially similar to the spatial and multimeric configuration of the wildtype HIV envelope gp160.

20. A method for the detection of HIV-specific antibodies in a sample comprising the following:

(i) providing a nucleotide sequence encoding an amino acid sequence comprising a protease recognition site;

(ii) providing a nucleotide sequence encoding for the HIV envelope glycoprotein precursor gp160, wherein said sequence lacks a functional wildtype gp120/gp41 proteolytic cleavage site;

(iii) inserting the nucleotide sequence of step (i) into the nucleotide sequence of step (ii) at a region corresponding to amino acids 645 to 673 of the transmembrane area of gp41, wherein said numbering scheme is based upon isolate HXB2, thereby creating a mutant HIV envelope gene;

(iv) cloning the mutant HIV envelope gene into a suitable expression vector and expressing said mutant HIV envelope gene in eukaryotic cell line to produce a recombinant mutant HIV envelope glycoprotein gp160 comprising said protease recognition site;

(v) subjecting the expression product of step (iv) to enzymatic digestion with a suitable protease thereby creating HIV gp140 envelope glycoprotein domains that retain their native oligomeric and glycosylated form;

(vi) isolating and purifying said HIV gp140 from the digestion mixture; and (vii) employing said isolated and purified gp140 as an antigen in a suitable immunoassay to detect HIV-specific antibodies.

21. An expression vector for expressing a glycosylated, oligomeric form of the gp120 env-glycoprotein of HIV comprising:

a recombinant vaccinia virus the genetic material of which comprises the mutant gene according to claim 1.

22. A composition comprising a mixture of recombinant truncated HIV envelope glycoprotein gp140 domains that retain their native oligomeric and glycosylated form comprising the following: at least one HIV envelope glycoprotein fragment, wherein said fragment comprises the gp120 domain, a portion of the amino terminus of gp41, said portion ranging in length from 131 to 165 amino acids, a non-functional wildtype gp120/gp41 proteolytic cleavage site, and a portion of a protease recognition site that remains following proteolytic cleavage, said fragment displaying an approximate molecular weight of 140 kDa as determined by SDS-PAGE and a tertiary and quaternary configuration that is substantially similar to that displayed by the native HIV envelope glycoprotein.

23. An isolated oligomeric and glycosylated ectodomain of the HIV env-glycoprotein, said ectodomain having an N-terminal end and a C-terminal end and having aphysicochemical configuration substantially similarto the physicochemical configuration of a native ectodomain of said HIV env-glycoprotein comprising:

a gp120 domain of the HIV env-glycoprotein comprising said N-terminal end of said isolated ectodomain; and a fragment of a gp41 domain of said HIV env-glycoprotein, said gp41 fragment comprising 148 amino acids and further comprising said C-terminal end of said isolated ectodomain.

* * * * *

UNITED STATES PATENT AND TRADEMARK OFFICE
CERTIFICATE OF CORRECTION

PATENT NO. : 6,140,059

DATED : October 31, 2000

INVENTOR(S) : Schawaller

It is certified that error appears in the above-identified patent and that said Letters Patent are hereby corrected as shown below: ON THE TITLE PAGE Item [54] of the face of Letters Patent, the word "Virsus" should be "Virus".

Signed and Sealed this

Eighth Day of May, 2001

*Attest:*

NICHOLAS P. GODICI

*Attesting Officer*      *Acting Director of the United States Patent and Trademark Office*